United States Patent [19]

Nemeth

[11] 4,107,292

[45] Aug. 15, 1978

[54] STABLE WATER DISPERSIONS OF ENCAPSULATED PARATHION

[75] Inventor: Harold C. Nemeth, Chicago, Ill.

[73] Assignee: Akzona Incorporated, Asheville, N.C.

[21] Appl. No.: 769,362

[22] Filed: Feb. 16, 1977

Related U.S. Application Data

[63] Continuation of Ser. No. 457,152, Apr. 1, 1974, abandoned, which is a continuation-in-part of Ser. No. 230,935, Mar. 1, 1972, abandoned.

[51] Int. Cl.$^2$ ............................................. A01N 9/36
[52] U.S. Cl. ..................................... 424/78; 424/32; 424/200; 424/213; 424/216; 424/218; 424/224; 424/225; 424/361
[58] Field of Search .................... 424/213, 218, 32, 78

[56] References Cited

U.S. PATENT DOCUMENTS

| 3,074,845 | 1/1963 | Geary .............................. 424/32 X |
| 3,212,967 | 10/1965 | McFadden ........................ 424/78 |
| 3,577,515 | 5/1971 | Vandergaer ...................... 424/32 |
| 3,594,151 | 7/1971 | Sprayberry et al. ............ 424/363 X |
| 3,959,464 | 5/1976 | De Savigny ..................... 424/78 |

OTHER PUBLICATIONS

Kelco Technical Bulletin (DB#18) (1971). The Condensed Chemical Dictionary, 8th ed. p. 495 (1971).

*Primary Examiner*—Leonard Schenkman
*Attorney, Agent, or Firm*—Francis W. Young; Robert F. Green; H. Walter Haeussler

[57] ABSTRACT

Disclosed herein are aqueous dispersions of polymer-encapsulated insecticides (e.g., phosphorothioates and phosphorodithioates) wherein xanthan gum is used as a dispersing agent. It has been found that by use of the xanthan gum, the aqueous dispersions are highly stable, even for periods as long as two years or more.

8 Claims, No Drawings

STABLE WATER DISPERSIONS OF ENCAPSULATED PARATHION

REFERENCE TO RELATED APPLICATIONS

The present invention is a continuation of application Ser. No. 457,152, Apr. 1, 1974 now abandoned which in turn is a continuation-in-part of Ser. No. 230,935, filed Mar. 1, 1972 now abandoned.

RELATED PRIOR ART

The following prior art patents are of interest: U.S. Pat. Nos. 3,464,926; 3,492,380; 3,607,776; and 3,717,452. British Pat. No. 1,091,141, published Nov. 15, 1967, is also of interest.

BACKGROUND OF THE INVENTION

Various insecticides for agricultural uses are known to be highly toxic to most species of insects and mites. However, many of these same materials (e.g., phosphorothioates and phosphorodithioates) are poisonous to higher animals including man, and there are many reported cases of injury and even death to workers in areas sprayed with poisonous insecticides. Lethal doses can be inhaled or absorbed through the skin.

In recent developments, many of the poisonous insecticides and fungicides have been encapsulated with polymers, especially polyamides. For example, methyl parathion has been encapsulated in a mixed polyamide-polyurea polymeric skin and the resulting capsules are commercially available as aqueous dispersions (e.g., Penncap M, by Pennwalt Corporation). Encapsulation is extremely significant from the standpoint of safety in the handling of these materials in that the capsules can be safely dispersed in water and applied by spray apparatus in the form of aqueous dispersions. Unfortunately, most of the insecticides which would benefit from encapsulation are also heavier than the surrounding aqueous dispersion media and, therefore, the capsules tend to settle out quickly, i.e., the dispersions tend to "break" soon after formulation to form two distinct phases or layers. The upper layer is generally clear and is believed to consist essentially of portions of the carrier liquid. The lower layer is generally opaque and constitutes the original dispersion minus some of the carrier liquid which has separated to form the upper clear liquid level. Finally, after standing, portions of the insecticide capsules generally separate from the lower dispersion phase and settle on the bottom of the container forming a third phase. Once settled, the capsules in this third layer tend to adhere to one another and cannot be easily redispersed in the field because only simple mixing equipment is generally available to most users under these conditions. This lack of redispersibility prevents these safer encapsulated forms of the insecticides from being uniformly applied by agricultural spray applicators. This is a serious disadvantage because in one area of a field, for example, the amount of material applied may be insufficient to give good control over the insect pest, whereas in other areas of the same field, the amount applied may be overdone to the point that toxicity problems arise.

What is needed to reduce present difficulties and to permit wide use of the safer encapsulated insecticides is a means for forming the insecticide capsules into essentially stable aqueous dispersions thereby minimizing amounts of material which must be redispersed. But, recognizing that even the best present dispersions tend to undergo some separation upon standing for prolonged periods, a dispersing agent is needed which not only forms a relatively stable dispersion but also interacts with the capsules to minimize packing in sedimentary layers resulting from settling, and permit the capsules to be easily redispersed using relatively simple mixing equipment. Surprisingly, these objects and advantages are obtained by my invention as described below.

DESCRIPTION OF THE INVENTION

The disadvantages described above which are inherent in aqueous dispersions of encapsulated insecticide formulated by conventional methods are overcome by employing in the dispersion from about 0.1 to about 0.5% (based on the weight of the total dispersion) of a xanthomonas hydrophilic colloid, more commonly known as xanthan gum. Accordingly, the invention is a highly stable aqueous dispersion for agricultural spraying wherein the active agricultural ingredient to be disseminated is a phosphorothioate insecticide which is a thio or dithio phosphate ester of phosphoric acid. Examples of the mono thio esters include methyl and ethyl parathion. The dithio esters are exemplified by Malathion (0,0-dimethyl-S-1,2-di(ethoxycarbamyl)ethylphosphorodithioate) and Diazinon 0,0-diethyl-0-(2-isopropyl-4-methyl-6-pyrimidinyl)phosphorothioate).

The phosphorothioate insecticides useful in the invention are also characterized in that they have a specific gravity of at least 1.05. To minimize health problems as well as to improve the ease of handling, the insecticide is encapsulated in a skin consisting essentially of cross-linked polyamide, polyurea, or mixtures thereof to form a plurality of globules or capsules which have the tendency described above, to separate when suspended in an aqueous medium. To retard separation and promote redispersion of the capsules, a xanthan gum colloid is employed. It is the incorporation of the xanthan gum which overcomes present formulation problems, results in a stable aqueous dispersion, and permits easy redispersion by relatively gentle agitation of the small amounts of capsules which may have formed a sedimentary layer at the bottom of the storage container.

While the mechanism by which the xanthan gum confers its benefits is not understood, the relative stability and redispersibility (particularly after long periods of standing, as from early in one growing season to late in the succeeding season) of the aqueous dispersions is highly surprising in view of the fact that a variety of commonly employed dispersing agents, e.g., gum karaya, gum tragacanth, locust bean gums, sodium alginate, methyl cellulose, maltose, pre-gelatinized starch, gum arabic, carageenan gum, agar, etc., were found to be ineffective either in stabilizing aqueous dispersions of the encapsulated insecticides, or in providing easy redispersion of settled material. Another advantage of the xanthan gum reagent is that very small amounts of reagent (e.g., 0.1% by weight of the total composition) have been found to stabilize relatively high loadings (e.g., 40 weight percent) of the insecticide capsules thus permitting manufacturers of the aqueous dispersions to prepare relatively concentrated dispersions while using only small (and highly economical) amounts of xanthan gum.

In preparing aqueous dispersions of the invention, it has been found that small amounts of xanthan gum within the narrow range of from 0.1% to 0.5% are sufficient to stabilize aqueous dispersions containing from about 1 to about 40% solids. For purposes of the present specification, the term "percent (%)" is based upon the total weight of the formulation. "Percent solids" or "solids loading" is the weight percent of capsules present and is determined by separating the insecticide capsules from the water and other ingredients present in the liquid phase and determining the weight of the dry capsules which is equal to the weight of the polymeric skin plus the encapsulated insecticide. A "stable" aqueous dispersion is one where nonseparation is discernable immediately after formulation and up to 24 hours thereafter, and where after 2½ years, at least 95% of the capsules remain dispersed based on visual observation. A dispersion which is "readily redispersable", such as in the present invention, is one wherein even after prolonged standing (e.g., at least 2 years), any material which has separated and formed a third phase on the bottom of the dispersion container, is redispersable by gentle agitation. For samples contained in 4 to 8 oz. sample bottles, redispersion can be accomplished in 5 seconds or less just by manual shaking of the bottle.

With the above definitions in mind, it has been found that 0.1% xanthan gum is sufficient to stabilize 40% solids or more with the advantages set forth above. At 30% and 0.1% xanthan gum, a small amount of separation (e.g., 15%) is observed after 24 hours. At solids levels below 30% (e.g., 15%), the dispersions are less stable where the amount of gum employed is very small, i.e., use of small amounts of gum is of use primarily in stabilizing high solids loadings. Similarly, at 0.2% gum concentration, medium levels of solids loading (e.g., 15%) were found to be stable. At gum concentrations of 0.3–0.5%, solids loadings as low as 1% are stable. To form stable dispersions by using low concentrations of gum (e.g., 0.3%) as compared to common practise, it is necessary simply to increase the solids loading until stability is achieved, it being understood from the above examples that the stability at high solids loading can be achieved with low gum levels.

Phosphorothioate insecticides which may be employed are further exemplified by the following compounds which are indicative of the wide range of suitable insecticides for which this invention is of value. The compounds are listed by their generic names followed by their trade names in parenthesis:

0,0-dimethyl-S-1,2-di(ethoxycarbamyl)ethylphosphorodithioate (Malathion); 0,0-diethyl-S-[4-oxo-1,2,3-benzotriazin-3(4H)-ylmethyl]-phosphorodithioate (Azophosethyl); 0,0-diethyl-S-[2-(ethylthio)-ethyl]-phosphorodithioate (Disulfoton); S-[(p-chlorophenyl)-thiomethyl]-0,0-diethylphosphorodithioate (Carbophenothion); S-[(p-chlorophenyl)thiomethyl]-0,0-dimethylphosphorodithioate (Methyltrithion); 0,0,0',0'-tetraethyl-S,S-methylenediphosphorodithioate (Ethion); 0,0,0',0'-tetramethyl-0,0'-thiodi-p-phenylenephosphorothioate (Abate); 0,0-dimethyl-S-(N-methylcarbamoylmethyl)phosphorodithioate (Dimethoate); S-[(ethoxycarbonyl)methylcarbamoyl]-methyl-0,0-diethylphosphorodithioate (Mercarbam); S-[(4,6-diamino-s-triazin-2-yl)methyl]-0,0-dimethylphosphorodithioate (Menazon); S,S-bis(0,0-diethylphosphorodithioate) (Delnav); 0,0-diethyl-0-para-nitrophenylphosphorothioate (Parathion); 0,0-dimethyl-0-para-nitrophenylphosphorothioate (Methyl Parathion); 0,0-dimethyl-0-(4-nitro-m-tolyl)phosphorothioate (Sumithion); 0,0-dimethyl-0-(3-chloro-4-nitrophenyl)phosphorothioate (Chlorothion); 0-(2-chloro-4-nitrophenyl)-0,0-dimethylphosphorothioate (Dicapthon); 0,0-diethyl-0-(2-isopropyl-4-methyl-6-pyrimidinyl) phosphorothioate (Diazinon); 0,0-diethyl-0-(2-ethylthio)ethylphosphorothioate and 0,0-diethyl-S-(2-ethylthio)ethylphosphorodithioate (Demeton); Mixture of 0,0-dimethyl-2-(2-ethylthio) phosphorothioate and 0,0-dimethyl-S-(2-ethylthio)phosphorodithioate (Methyldemeton); S-[2-(ethylsulfinyl)ethyl]-0,0-dimethylphosphorothioate (Meta Systox-R); dimethylethylmercaptoethylphosphorothioate (Meta Systox-I); 0,0-diethyl-0-2-pyrazinylphosphorothioate (Zinophos); 0,0-dimethyl-0-[4-(methylthio)-m-tolyl]phosphorothioates (Fenthion); 0,0-diethyl-0-[p-(methylsulfinyl)phenyl]-phosphorothioates (Fensulfothion); 0,0-diethyl-0-(2,4-dichlorophenyl)phosphorothioate) (UC-13); 0,0-dimethyl-0-(2,4,5-trichlorophenyl)phosphorothioate (Ronnel); 0,0-diethyl-0-(3,5,6-trichloro-2-pyridyl)phosphorothioate (Dursban); 0,0-diethyl-0-3-chloro-4-methyl-2-oxo-2H-1-benz pyran-7yl phosphorothioate (Co Ral); 0-ethyl-S,S-dipropylphosphorodithioate (Mocap).

The stable aqueous dispersions are prepared by admixing insecticide capsules with water until the desired loading is obtained, e.g., from 1 to about 40 weight percent based on the total composition weight and preferably from 10 to about 40 weight percent. Where the material is to be diluted prior to application and also to avoid shipment of large volumes of water, it is desirable to have a solids loading of from 20 to 40%, and preferably about 30%. Soon after forming the capsule/water admixture, and before the capsules have had time to cake together, the xanthan gum dispersing agent is added with sufficient stirring to form a homogenous dispersion. As discussed above, the amount of gum employed is from 0.1 to about 0.5 weight percent. For relatively high solids loadings, e.g., 30–40%, the amount of gum employed can be as little as 0.1% which certainly constitutes a commercial advantage. However, for lower solids levels, e.g., less than 15%, the dispersions may be unstable. This can be corrected by raising the gum level to 0.3% or more, or by increasing the solids content.

Another method of forming the dispersions involves addition of the xanthan gum directly to commercially available formulations such as Penncap M (Pennwalt Corporation) aqueous dispersions of polyamide-polyurea encapsulated methyl parathion. In this case, the material as received may be "caked" and may require strenuous mixing to initially redisperse the capsules. However, once dispersed, the xanthan gum is added as described above to form a stable aqueous dispersion.

Xanthan gum as employed in the present invention includes the available commercial forms of gum such as Keltrol (Kelco), Kelzan (Kelco), and Biopolymer (General Mills). Also of interest are the materials described in U.S. Pat. No. 3,717,452 of which columns 2, 3, and 4 are expressly incorporated into the present specification by reference to illustrate a method of preparing the xanthan gum reagent. More specifically, the xanthan gum can be described as a polysaccharide, although as stated above and shown in the Examples, conventional dispersants including other polysaccharides were not found to be effective in forming stable aqueous dispersions. Xanthan gum is a complex polysaccharide having a molecular weight of over one million, is linear in structure with D-linked units containing D-glucose, D-mannose, and D-glucuronic acid in a ratio of approximately 2.8:3.0:2.0 with one D-mannose side-chain for every eight sugar residues and one D-glucose side-chain for every sixteen sugar residues. Gum derivatives can also be employed as where the xanthan gum is partially acetylated and/or contains the reaction product of pyruvic acid with one or more D-glucose side-chains.

The preparation of capsules of polymer-encapsulated insecticides is well known. See, for example, U.S. Pat. No. 3,577,515 (Pennwalt Corporation) which describes suitable methods involving interfacial polymerization. The actual methods used to form capsules wherein the skins are cross-linked polyamide, polyurea, or mixed polyamide-polyurea are set forth in Examples 11, 12, 14, and 17) from the above patent which are hereby incorporated by reference into the present application. Generally, the interfacial method of polymer encapsulation of an insecticide involves the steps of forming an oil-in-water emulsion, with the insecticide (e.g., methyl parathion) forming the discontinuous hydrophobic phase. Prior to formation of the emulsion, the appropriate monomers are dispersed in separate phases so that upon forming the emulsion, the monomers react at the interface of the oil phase droplets with the continuous aqueous phase thereby forming a polymeric encapsulating skin around the insecticide droplet. Subsequently, the capsules may be separated from the aqueous residue and force further processing, as by drying, prior to redispersion in an aqueous carrier phase.

To further exemplify the method of interfacial polymerization, where the polymer skin is to be a polyamide, acid chloride such as sebacoyl chloride, adipoyl chloride, and azeloyl chloride may be dissolved in the oil phase with diamines such as ethylene diamine, toluene diamine, and hexamethylene diamine being dispersed in the aqueous phase. To form a polyurea skin, the oil phase may contain phosgene or a diisocyanate with the aqueous phase containing a diamine or polyol. A mixed polyamide-polyurea skin may be obtained by dispersing both an acid chloride and a diisocyanate in the oil phase and employing a diamine in the aqueous phase. The polymer skin is cross-linked by employing tri- or higher functional amines (polyalkylenepolyamine) or issocyanates as part of the monomeric system. For example, diethylenetriamine, triethylenetetramine and polymethylenepolyphenylisocyanate, e.g., Papi (Upjohn), can be employed. Examples of other suitable monomers are described in U.S. Pat. No. 3,577,515, at column 7, lines 55 and following through column 8, line 28, which material is hereby incorporated by reference into the present specification. The following Examples are set forth to illustrate the present invention in its various embodiments.

PREPARATION OF INSECTICIDE CAPSULES

In all of the examples to follow, the reactions were carried out in a 1-liter resin flask fitted with a Kraft Non-Aerating Stirrer and 2 dropping funnels. All reactions were carried out at ambient temperature and pressure. To facilitate the formation and increase the stability of the initial oil-in-water suspension during the encapsulation process, a dispersing aid, such as Gelvatol 20/90 (Monsanto) a polyvinyl alcohol resin was used in the aqueous phase at a level of 0.5%. To reduce foaming, a defoaming agent, e.g., Antifoam B (Dow Corning) was also employed.

EXAMPLE 1

In this example, an organic liquid pesticide, Malathion was encapsulated in a polyamide-polyurea skin cross-linked by employing a polyfunctional isocyanate for the polyurea reaction.

In flask
450 ml. aqueous 0.5% Gelvatol 20/90 Solution
9 drops Antifoam B
In the 1st funnel
44.7 g. Malathion (technical grade)
19.5 g. azeloyl chloride
3.0 g. polymethylenepolyphenylisocyanate (Papi-Upjohn)
In the 2nd funnel
30 g. diethylenetriamine
15 g. sodium carbonate monohydrate
150 ml. distilled water The flask, charged as indicated above, was agitated at 6–7,000 r.p.m. and contents of the first and second funnels were added rapidly and consecutively thereto. Following addition, the agitation speed was reduced and continued for approximately one hour. During the addition and agitation stages, small droplets were clearly visible in the reaction mixture and the reaction proceeded rapidly to produce the insecticide capsules. After standing, the capsules settled to the bottom of the reaction vessel and were additionally concentrated by centrifugation and the supernatant was removed. The capsules were washed twice with deionized water with removal of the liquid phase following centrifugation. Subsequently, the capsules were air dried at room temperature on a filter paper. When suspended in a water slurry, microscopic examination revealed that the capsules ranged in diameter from about 5–40 microns with the majority being in the 20–30 micron range. For use in pesticide preparations, these pesticide-containing capsules can release their contents by gradual diffusion, or by leaching action.

EXAMPLE 2

Malathion was encapsulated as in Example 1. The polymeric skin was a polyamide using a trifunctional amine and a trifunctional acid chloride as cross-linking agent.

In the flask
450 ml. aqueous 0.5% Gelvatol 20/90 Solution
9 drops Antifoam B
In the 1st funnel
18 g. sebacoyl chloride
4.5 g trimesoyltrichloride (1,3,5-benzenetricarboxylic acid chloride)
60 g. Malathion
In the 2nd funnel
18 g. ethylenediamine
3.1 g. diethylenetriamine
15 g. sodium carbonate monohydrate
75 ml. distilled water Agitation was begun at about 4–6,000 r.p.m. and the contents of the first funnel were rapidly added to the reaction flask. The stirring rate was reduced to about 50% and the contents of the second funnel were rapidly added. Stirring was continued two minutes then the reaction flask was allowed to stand overnight. The capsules were separated by filtration, were washed with deionized water and air dried.

EXAMPLE 3

In this example, Malathion was encapsulated in a cross-linked polyurea skin using a polyfunctional isocyanate material (understood to comprise chiefly a compound containing 3 isocyanate groups) alone as one of the complementary intermediates which also provided the significant cross-linking function.

The flask and funnels were charged as follows:
In the flask
400 ml. aqueous 0.5% Gelvatol 20/90 Solution
8 drops Antifoam B
In the 1st funnel
100 g. Malathion
33.3 g. polymethylenepolyphenylisocyanate (Papi-Upjohn)
In the 2nd funnel
15.7 g. sodium carbonate monohydrate
15.0 g. ethylenediamine
15.0 g. diethylenetriamine Agitation in the flask was started and increased to about 5,000-7,000 r.p.m., the contents of the first funnel were added rapidly, the stirring rate reduced and the contents of the second funnel were added. Stirring at a reduced rate was continued for two hours, then the reactants were allowed to stand for two hours. The resulting capsules were concentrated by centrifugation, the supernatant was removed and the capsules were washed with deionized water. This process was repeated and the capsules air dried on filter paper.

EXAMPLE 4

In this example, Malathion was encapsulated in a cross-linked polyamide.
In the flask
400 ml. 0.5% Gelvatol 20/90 Solution
6 drops Antifoam B
In the 1st funnel
65 g. Malathion
6.7 g. sebacoyl chloride (Eastman)
In the 2nd funnel
2.2 g. diethylenetriamine
3.8 g. 1,6-hexamethylenediamine
18 g. sodium carbonate monohydrate
100 ml. distilled water The reaction flask was charged as indicated. Moderate agitation was begun and the contents of the first funnel were added rapidly to the reaction flask. The stirring rate was reduced, the contents of the second funnel were added rapidly and stirring was continued for an additional 25 minutes. After standing another hour, the reaction mixture was filtered, and the capsules washed twice with deionized water. The supernatant was decanted following centrifugation during the wash procedure, and the capsules were air dried.

EXAMPLE 5

In this example, Malathion was encapsulated in a cross-linked polyurea skin formed using toluene 2,4-diisocyanate as a major ingredient and only a small amount of a polyfunctional isocyanate as a cross-linking agent.
In the flask
400 ml. 0.5% aqueous Gelvatol 20/90 Solution
8 drops Antifoam B
In the 1st funnel
100 g. Malathion
30 g. toluene 2,4-diisocyanate
3.5 g. polymethylenepolyphenylisocyanate (Papi-Upjohn)
In the 2nd funnel
15.0 g. ethylenediamine
15.0 g. diethylenetriamine
15.7 g. sodium carbonate monohydrate
133 g. distilled water The flask was charged as indicated, moderate agitation was started and the contents of the first funnel were rapidly added to the reaction. The stirring rate was reduced and the contents of the second flask were added. The stirring rate was reduced again and continued for 30 minutes. After standing one hour, the capsules were well packed down and the supernatant was readily decanted. The capsules were washed twice with deionized water, the supernatant being decanted following centrifugation, and the capsules were air dried.

EXAMPLE 6

In this example, oil-in-water encapsulation was carried out to achieve a copolymer skin (polyamide-polyurea), cross-linking being achieved with polymethylenepolyphenylisocyanate. The pesticide encapsulated was methyl parathion.
In the flask
450 ml. 0.5% Gelvatol 20/90 Solution
9 drops Antifoam B
In the 1st funnel
44.7 g. methyl parathion - 80% Tech. Grade (Kerr McGee)
19.5 g. azeloyl chloride
3.0 g. polymethylenepolyphenylisocyanate (Papi-Upjohn)
In the 2nd funnel
30 g. diethylenetriamine
15 g. sodium carbonate monohydrate
150 ml. distilled water
Procedure The flask was charged as indicated above, agitation increased to 3-4,000 r.p.m., the contents of the first and second funnels were added rapidly and consecutively, the speed was reduced and continued for an additional hour. After standing overnight, the capsules were concentrated by centrifugation and the supernatant removed. The capsules were washed twice with deionized water with removal of the liquid following centrifugation.

STABILITY STUDIES

The following examples illustrate the stability of dispersions of encapsulated insecticides using xanthan gum as well as other substances as the dispersing agent. In grading the stability of the dispersions, a "stable" dispersion is one in which no phase separation appears during the first 24 hours following formation. A dispersion showing "slight separation" is one having two phases with the dispersion phase occupying at least 85% of the volume of the container employed. In the following examples, 8-ounce sample bottles were used as containers. The volume percentage is easily determined by measuring the total height of the sample (assuming essentially uniform cross-section) and dividing this figure into the height of the dispersion layer (which includes any sediment which may be on the bottom of the sample bottle). The resulting decimal is then multiplied by 100 to obtain a percentage figure such as those set forth in Table III. A "moderately" separated dispersion is one wherein the dispersion phase has a volume of from 85 to 75%. A sample is said to be completely separated where the dispersion layer occupies less than 75% by volume of the sample being measured.

While the stability of dispersions is highly important, another highly important factor is the ease with which dispersions in various degrees of separation can be redispersed to form a single phase system, i.e., even though separation has occurred, a sample could still have commercial utility if it was readily redispersible so that ordinary stirring apparatus could be employed. Redispersibility is particularly important in determing the utility of material which may not be used during one growing season but would be used in the next season, and could, therefore, be one or more years old at the time of use. In Table III, the redispersibility of a number of samples was determined after 2½ years. In all of these samples, there was sedimentation of the insecticide capsules. The amount of sedimentation varied widely among the samples. To determine redispersibility, each sample was shaken manually for five seconds after which time an estimate was made of the amount of material in the sedimentary layer which had become redispersed, i.e., the extent of diminution of the sedimentary layer was estimated. A poor rating was 10–15% redispersion; fair was 15–25%; good was 25–50%; very good was 50–99%; and excellent was essentially complete redispersion with no sediment being visible at the end of the five-second period.

The time necessary to obtain complete redispersion was also determined by shaking the samples until the sediment layer was no longer visible.

The experimental work is described in more detail in the following examples.

EXAMPLE 7

Capsules prepared in the preceding examples were dispersed in water using varying amounts of xanthan gum (Kelzan) as indicated below in Table I. In preparing the suspension, the gum was pre-mixed with deionized water and the dried capsules were then added and the resulting suspension was agitated for 20 minutes to simulate conditions which would be employed in the commercial preparation of aqueous dispersions.

The numbers in Table I refer to the percent by weight of the total composition formed by each ingredient. As can be seen, with the exception of run C, all dispersions employing the xanthan gum were stable, and remained so even after 24 hours. In run C, the dispersion was initially stable and was suitable for application by commercial spraying apparatus. After 24 hours, settling was observed. However, this is correctable by increasing the solids loading (as by decanting off a portion of the aqueous suspending media) or alternatively by adding more of the xanthan gum. This is illustrated in run D where the gum level is 0.3% rather than 0.2% as in run C. The 0.3% level of run D is still relatively small in comparison with the relatively large amounts of dispersing agents customarily employed in forming aqueous dispersions. After 4 weeks, all xanthan gum samples showed slight separation, except for run A, which showed none. These samples (C, D, E, G, I, K, M) could be readily redispersed by gentle agitation in contrast to the control samples (B, F, H, J, L, N) which showed complete separation and were difficult to redisperse.

TABLE I*

| Materials Source | Run A | Run B | Run C | Run D | Run E | Run F | Run G | Run H | Run I | Run J | Run K | Run L | Run M | Run N |
|---|---|---|---|---|---|---|---|---|---|---|---|---|---|---|
| Example 1 | 20.00 | 20.00 | — | — | — | — | — | — | — | — | — | — | — | — |
| Example 2 | — | — | 20.00 | 20.00 | 20.00 | 20.00 | — | — | — | — | — | — | — | — |
| Example 3 | — | — | — | — | — | — | 20.00 | 20.00 | — | — | — | — | — | — |
| Example 4 | — | — | — | — | — | — | — | — | 20.00 | 20.00 | — | — | — | — |
| Example 5 | — | — | — | — | — | — | — | — | — | — | 20.00 | 20.00 | — | — |
| Example 6 | — | — | — | — | — | — | — | — | — | — | — | — | 20.00 | 20.00 |
| Deionized Water | 77.70 | 80.00 | 79.80 | 79.70 | 79.60 | 80.00 | 79.70 | 80.00 | 79.70 | 80.00 | 79.70 | 80.00 | 79.70 | 80.00 |
| Xanthan Gum | 0.30 | — | 0.20 | 0.30 | 0.40 | — | 0.30 | — | 0.30 | — | 0.30 | — | 0.30 | — |
| Initial Appearance | Stable | Sep. | Stable | Stable | Stable | Sep. | Stable | Sep. | Stable | Sep. | Stable | Sep. | Stable | Sep. |
| Appearance 24 Hours | Stable | Sep. | Sl. Sep. | Stable | Stable | Sep. | Stable | Sep. | Stable | Sep. | Stable | Sep. | Stable | Sep. |
| Appearance 4 Weeks | Stable | Sep. | Sep. | Sl. Sep. | Sl. Sep. | Sep. | Sl. Sep. | Sep. | Sl. Sep. | Sep. | Sl. Sep. | Sep. | Sl. Sep. | Sep. |

*All numerical values are expressed as percent by weight

EXAMPLE 8

This example illustrates the stability of various formulations of a commercially available material, Penncap M. Preparation of this material is described in U.S. Pat. No. 3,577,515 to Pennwalt Corporation. As received, the material was a 30% aqueous dispersion. However, the insecticide capsules had settled badly tending to form a rather firm cake and were dispersed only with difficulty after vigorous shaking by hand.

After redispersing the capsules, the material was diluted with deionized water to various solid loadings. Each solids level was matched against several levels of xanthan gum (Kelzan). The results are set forth below in Table II. For solid concentrations in excess of 30%, the Penncap M was concentrated by decanting off part of the supernatant from the untreated Penncap M. In Table II, the viscosity measurements were determined at 24° C. with a Brookfield Viscometer (RVF) using a #3 spindle rotating at 10 r.p.m. This viscosity test conforms to several of the specifications set forth in ASTM method D2196-68: Rheological Properties of Non-Newtonian Materials.

TABLE II

| Run | Gum Level (%) | Solids Level (%) | Initial Stability | Initial Viscosity (cps) | Stability After 24 Hours | Viscosity (cps) After 24 Hours | Stability After 6 Weeks |
|---|---|---|---|---|---|---|---|
| 1 | 0.5 | 15 | Stable | 3050 | Stable | 3400 | Stable |
| 2 | 0.5 | 6.8 | Stable | 1950 | Stable | 2175 | Stable |
| 3 | 0.5 | 1.36 | Stable | 1650 | Stable | 1650 | Stable |
| 4 | 0.3 | 1.36 | Stable | 550 | Stable | 450 | Sl. Sep. |

TABLE II-continued

| Run | Gum Level (%) | Solids Level (%) | Initial Stability | Initial Viscosity (cps) | Stability After 24 Hours | Viscosity (cps) After 24 Hours | Stability After 6 Weeks |
|---|---|---|---|---|---|---|---|
| 5 | 0.3 | 6.8 | Stable | 800 | Stable | 880 | Sl. Sep. |
| 6 | 0.3 | 15 | Stable | 1200 | Stable | 1280 | Stable |
| 7 | 0.1 | 1.36 | Unstable | — | — | — | — |
| 8 | 0.1 | 6.8 | Unstable | — | — | — | — |
| 9 | 0.1 | 15 | Unstable | — | — | — | — |
| 10 | 0.2 | 1.36 | Stable | 200 | Sep. | — | Unstable |
| 11 | 0.2 | 6.8 | Stable | 250 | Sep. | — | Unstable |
| 12 | 0.2 | 15 | Stable | 1700 | Stable | 1740 | Sl. Sep. |
| 13 | 0.1 | 40 | Stable | 1180 | Stable | 1250 | Stable |
| 14 | 0.0 | 40 | Unstable | 100 | — | — | — |
| 15 | 0.3 | 40 | Stable | 7450 | Stable | 7920 | Stable |
| 16 | 0.1 | 30 | Stable | 375 | Sl. Sep. | 375 | Sl. Sep. |
| 17 | 0.5 | 30 | Stable | 6500 | Stable | 6800 | Stable |
| 18 | 1.0 | 30 | Stable | +10,000 | Stable | +10,000 | Stable |

From Table II, it can be seen that Penncap M without a dispersing aid was stabilized by the xanthan gum. As discussed above, where the gum concentration is less than about 0.3%, there is some settling out and lack of stability. This can be corrected by increasing the solids loading of the gum concentration. However, even where the dispersions were unstable, if desired, they are easily redispersed with mild manual agitation or with the use of conventional mechanical stirring apparatus such as is frequently employed in agricultural sprayers. The ease of redispersion should be contrasted with the original Penncap M sample as received.

EXAMPLE 9

This example illustrates the superior dispersing ability of xanthan gum in comparison with other commonly employed suspending or dispersing agents. Using commercially available Penncap M, as in Example 8, the capsules were redispersed from their caked form. A large number of 8-ounce sample bottles were filled with (on a weight basis) 99.5 parts of the redispersed Penncap M material and 0.5 parts of a dispersing agent as set forth in Table III below. Each sample was stirred mechanically at 800–1000 r.p.m. for 20–30 minutes at room temperature.

Table III below describes the extent of separation in each sample 24 hours after preparation. After two weeks, an attempt was also made to redisperse the samples. These results are also shown in Table III. A "good" result in the column labelled "Two Week Redispersibility" is one in which most of the Penncap M was redispersed after five seconds shaking by hand. A "poor" result was given to a sample which still showed some (i.e., 10% or more) solids settling after shaking. Any sample showing poor redispersibility would probably be unsuitable for use in stirring apparatus normally available with commercial agricultural spray applicators.

Following the two-week redispersibility, the samples were stored on a laboratory bench for 2½ years where they were subjected to normal variations in room temperature (i.e., 20–30° C.). At the end of this time, stability, ease of redispersion, and complete redispersibility were determined.

TABLE III

| Run | Material | After 24 Hours | 2 Week Redispersibility Rating | After 2-½ Years % Dispersion Layer to Total Volume | Redispersibility Rating | Time Complete Redispersibility (in seconds) |
|---|---|---|---|---|---|---|
| 1 | Locust Bean Gum (Stein-Hall) | Complete Sep. | Good | — | — | — |
| 2 | Okra gum (Morning Star-Paisely) | Complete Sep. | Poor | 70.00 | Poor | 30 |
| 3 | Gum Arabic (Stein-Hall) | Complete Sep. | Poor | 56.45 | Poor | 90 |
| 4 | Tragacanth gum (Stein-Hall) | Slight Sep. | Good | — | — | — |
| 5 | Carrageenam gum (Stein-Hall, K-100) | Complete Sep. | Poor | 64.81 | Poor | 55 |
| 6 | Karaya gum (Stein-Hall, K-3) | Moderate Sep. | Good | 71.37 | Fair | 20 |
| 7 | Guar gum (Stein-Hall, A-20-D Jaguar) | No Separation | Stable | 60.00 | Fair | 20 |
| 8 | Agar (Difco) | Complete Sep. | Poor | 65.81 | Poor | 40 |
| 9 | Vegetable Lecithin (Eastman) | Complete Sep. | Poor | — | — | — |
| 10 | Slow Setting Pectin (Stein-Hall) | Complete Sep. | Poor | 60.45 | Poor | 25 |
| 11 | Citrus Pectin (Eastman) | Complete Sep. | Poor | 61.57 | Poor | 30 |
| 12 | Rapid Setting Pectin (Stein-Hall) | Complete Sep. | Poor | 53.06 | Poor | 25 |
| 13 | Lignin Sulfonate (Crown-Zellerbach, Orzan A) | Complete Sep. | Poor | 62.72 | Poor | 25 |
| 14 | Xanthan gum (Kelco, Kelzan) | No Separation | Stable | — | — | — |
| 15 | Gelatin (Knox) | Complete Sep. | Poor | — | — | — |
| 16 | Pre-gelatinized starch (Stein-Hall) | Slight Sep. | Poor | 85.49 | Fair | 110 |
| 17 | Modified tapioca starch (Stein-Hall) | Complete Sep. | Poor | 67.45 | Poor | 55 |
| 18 | Gelatin (Stein-Hall, gelatin 225) | Complete Sep. | Poor | 53.24 | Poor | 50 |
| 19 | Dispersable starch (Stein-Hall) | Complete Sep. | Good | — | — | — |
| 20 | Maltose (Fisher) | Slight Sep. | Good | 75.76 | Poor | 45 |
| 21 | Lactose (Fisher) | Complete Sep. | Poor | 72.00 | Poor | 55 |
| 22 | Carboxy gum ether (General Mills, Gendrix 307) | Complete Sep. | Poor | 57.65 | Poor | 25 |
| 23 | Carboxy alkyl gum (General Mills, XG-383S) | No Separation | Stable | 59.54 | Fair | 20 |
| 24 | Xanthan gum-high viscosity (General Mills) | No Separation | Stable | 94.50 | Exc. | 5 |
| 25 | Xanthan gum-low viscosity (General Mills) | No Separation | Stable | 94.37 | Exc. | 5 |

TABLE III-continued

| Run | Material | After 24 Hours | 2 Week Redispersibility Rating | % Dispersion Layer to Total Volume | Redispersibility Rating | Time Complete Redispersibility (in seconds) |
|---|---|---|---|---|---|---|
| 26 | Guar gum (General Mills-Gendrix 162) | Slight Sep. | Good | 65.32 | Poor | 25 |
| 27 | XG-458-S (General Mills) | No Separation | Stable | 68.72 | Poor | 30 |
| 28 | Methyl cellulose (Dow-Methocel 1000) | Complete Sep. | Good | — | — | — |
| 29 | Polyoxypropylene (Wyandotte-Pluronic F-127) | Complete Sep. | Poor | 48.56 | Good | 15 |
| 30 | Polyvinyl propylene (GAF) | Complete Sep. | Poor | 62.33 | Poor | 55 |
| 31 | Napthalene sulphonic acid (Rohm & Haas - Tanol SN) | Complete Sep. | Poor | 62.50 | Poor | 85 |
| 32 | Hydroxy ethyl cellulose (Hercules-Natrosol) | Complete Sep. | Good | 51.43 | Poor | 60 |
| 33 | Polyethylene glycol ester of stearic acid (Kessler - PEG 6000 Distearate) | Complete Sep. | Poor | 56.00 | Fair | 20 |
| 34 | Resin polymer (B.F. Goodrich - Carbopol 941)₃ | Complete Sep. | Poor | 58.21 | Poor | 45 |
| 35 | Resin polymer (B.F. Goodrich-Carbopol 934)₁ | Complete Sep. | Poor | 56.73 | Poor | 45 |
| 36 | Resin Polymer (B.F. Goodrich-Carbopol 940)₂ | Complete Sep. | Poor | 53.91 | Poor | 55 |
| 37 | Xanthan gum-food grade (Kelco-Keltrol) | No Separation | Stable | 95.53 | Exc. | 5 |
| 38 | Sodium alginate (Kelco-Kelgin XL) | Complete Sep. | Good | — | — | — |

₁The 0.5 parts of dispersing agent consisted of 0.1 part Carbopol 934, 0.3 part 7% NaOH in tap water and 0.1 part Ethomeen O/25 - a long chain ethoxylated amine produced by Armak Company.
₂Only 0.2 parts of dispersing agent were employed - 0.1 part polymeric resin - and 0.1 part Ethomeen O/25.
₃High molecular weight carboxy vinyl polymers.

From Table III, it can be seen that in runs 14, 24, 25 and 37, where xanthan gum was employed, a stable dispersion was formed. The xanthan gum dispersions showed no settling after 2 weeks time. After 2½ years, the samples showed little, if any, settling, i.e., well in excess of 90% of the insecticide capsules remained dispersed in each sample.

By contrast, from Table III, it can be seen that several of the materials tested, i.e., gum tragacanth, and General Mills XG-383S and XG-458S "worked" in the sense that while a stable dispersion was not prepared (i.e., each dispersion showed various degrees of settling), at least the settled materials did not cake together so that redispersion was difficult.

The guar gums (runs 7 and 26) present a special case in that one of the dispersions formed (run 7) initially appeared to be stable. However, it can be seen that after 2½ years, the material was badly settled with only 60% remaining dispersed, and that redispersibility was only "fair". By contrast, the small amount of material settled from the xanthan gum dispersions was completely redispersed after 5 seconds.

EXAMPLE 10

In addition to the stability studies described in Table III above, at the end of the 2½ year period, certain samples were analyzed to determine if the dispersing agent affected the insecticide content of the capsules. To make this determination on any particular sample, the sample was first placed in a vacuum oven at 70°-80° C. for up to four hours to remove water. Vacuum pressure was equivalent to about 25 inches of Hg. The resulting capsules were extracted (Soxlet extractor) using diethyl ether in which the methyl parathion is soluble. After removal of the ether, the residue was diluted and analyzed accordin to AOAC colorimetric procedure 24.132 and 4.188 (correction for p-nitrophenol). The results are set forth below in Table IV wherein the run number corresponds with the number in Table III. Samples analyzed for extraction in Example 10 were not also analyzed for 2½ year stability and redispersibility in Example 9. The run using gum arabic does not correspond with any of the runs of Table III and is believed to be aberrational, especially with regard to the figure of 110% shown in the far right-hand column of Table IV. From Table IV it can also be seen (far right-hand column) that the extracting power of the dispersing agents tested is relatively small.

TABLE IV

| Run | Dispersing Agent | Methyl Parathion Contained In Capsules | % of Control |
|---|---|---|---|
|  | none (control) | 18.99 | 100.00 |
| 1 | locust bean gum | 17.50 | 92.14 |
|  | gum arabic | 20.90 | 110.04 |
| 4 | gum tragacanth | 18.30 | 96.35 |
| 9 | lecitin | 15.70 | 82.66 |
| 15 | gelatin (Knox) | 18.00 | 94.77 |
| 19 | dispersible starch | 18.80 | 98.98 |
| 28 | methocel 100 cps | 18.40 | 96.88 |
| 33 | Kelgin XL (sodium alginate) | 18.30 | 96.35 |
| 14 | Kelzan (xanthan gum) | 18.48 | 98.67 |

What is claimed is:

1. An insecticidal composition consisting essentially of an aqueous dispersion of:
   (a) from about 1% to about 40% by weight of said composition of capsules of a member of the group consisting of a phosphoromonothioate and a phosphorodithioate insecticide encapsulated in a skin selected from the group consisting of a polyamide, a polyurea, and a mixed polyamide-polyurea cross-linked with a cross-linking agent selected from the group consisting of a polyalkylene polyamine and a polyfunctional isocyanate;
   (b) from about 0.1% to about 0.5% by weight of said composition of a xanthan gum dispersant for said capsules; and
   (c) balance water.

2. The composition of claim 1 in which the encapsulated insecticide is methyl parathion.

3. The composition of claim 1 in which the encapsulated insecticide is malathion.

4. The composition of claim 1 in which the polyalkylene polyamine is selected from the group consisting of diethylene triamine and triethylene tetramine.

5. The composition of claim 1 in which the polyfunctional isocyanate cross-linking agent is polymethylene polyphenyl isocyanate.

6. The composition of claim 1 in which the encapsulated insecticide is methyl parathion and the skin is a mixed polyamide-polurea cross-linked with polymethylene polyphenyl isocyanate.

7. An insecticidal composition consisting essentially of an aqueous dispersion of:
  (a) from about 1% to about 40% by weight of capsules of an insecticide selected from the group consisting of methyl parathion and malathion encapsulated in a skin of a cross-linked polyamide-polyurea polymer formed by the reaction of (1) an acid chloride selected from the group consisting of sebacoyl chloride, adipoyl chloride, and azeloyl chloride, and an isocyanate selected from the group consisting of polymethylene polyphenyl isocyanate and toluene diisocyanate, with (2) a polyamine selected from the group consisting of ethylene diamine, diethylene triamine, and hexamethylene diamine, and a mixture thereof;
  (b) from about 0.1% to about 0.5% by weight of a xanthan gum dispersant for said capsules; and
  (c) balance water.

8. An insecticidal composition consisting essentially of an aqueous dispersion of:
  (a) from about 1% to about 40% by weight of capsules of methyl parathion insecticide encapsulated in a skin of a cross-linked polyamide-polyurea polymer formed by the reaction of a mixture of sebacoyl chloride and polymethylene polyphenyl isocyanate with a mixture of ethylene diamine and diethylene triamine;
  (b) from about 0.1% to about 0.5% by weight of a xanthan gum dispersant for said capsules; and
  (c) balance water.

* * * * *